United States Patent

Brands et al.

[11] Patent Number: 5,965,747
[45] Date of Patent: Oct. 12, 1999

[54] CRYSTALLINE FORMS OF ANTIBIOTIC SIDE CHAIN INTERMEDIATES

[75] Inventors: Karel M. J. Brands, Hoboken; Ronald B. Jobson, East Brunswick, both of N.J.

[73] Assignee: Merck & Co., Inc., Rahway, N.J.

[21] Appl. No.: 09/102,449

[22] Filed: Jun. 22, 1998

Related U.S. Application Data

[60] Provisional application No. 60/052,197, Jul. 10, 1997.
[51] Int. Cl.$^6$ .................... C07D 207/08; C07D 207/12
[52] U.S. Cl. .................... 548/537; 548/541; 548/556
[58] Field of Search ..................... 548/537, 541, 548/556

[56] References Cited

U.S. PATENT DOCUMENTS 5,478,820  12/1995  Betts et al. ................... 514/210

FOREIGN PATENT DOCUMENTS

WO 97/06154   2/1997   WIPO .

*Primary Examiner*—Johann Richter
*Assistant Examiner*—Jane C. Oswecki
*Attorney, Agent, or Firm*—Sylvia A. Ayler; Mark R. Daniel

[57] ABSTRACT

Crystalline 2S-cis-3-[[(4-mercapto-2-pyrrolidinyl)carbonyl]-amino]benzoic acid and salts and solvates thereof are disclosed. Three different crystalline types are described.

7 Claims, 3 Drawing Sheets

CRYSTALLINE FORMS OF ANTIBIOTIC SIDE CHAIN INTERMEDIATES

RELATED APPLICATION

This application claims the benefit of Ser. No. 60/052,197 filed on Jul. 10, 1997.

BACKGROUND OF THE INVENTION

Crystalline forms of intermediates for carbapenem antibiotics are desirable from a stability and purity standpoint. These compounds facilitate the synthesis of carbapenem antibiotics on a commercial scale.

In the present invention, crystalline forms of the compound 2S-cis-3-[[(4-mercapto-2-pyrrolidinyl)carbonyl]-amino]benzoic acid have been discovered and characterized. Crystalline 2S-cis-3-[[(4-mercapto-2-pyrrolidinyl)carbonyl]-amino]benzoic acid and pharmaceutically acceptable salts and solvates thereof are disclosed. The compounds can generally be synthesized taking into account the disclosure of U.S. Pat. No. 5,478,820 granted on Dec. 26, 1995. This patent does not disclose the side chain in crystalline form.

SUMMARY OF THE INVENTION

Crystalline 2S-cis-3-[[(4-mercapto-2-pyrrolidinyl)carbonyl]-amino]benzoic acid as well as pharmaceutically acceptable salts and solvates thereof are disclosed.

BRIEF DESCRIPTION OF THE DRAWINGS

The invention is described in connection with the following drawings, of which.

DETAILED DESCRIPTION OF THE INVENTION

Figure 1:
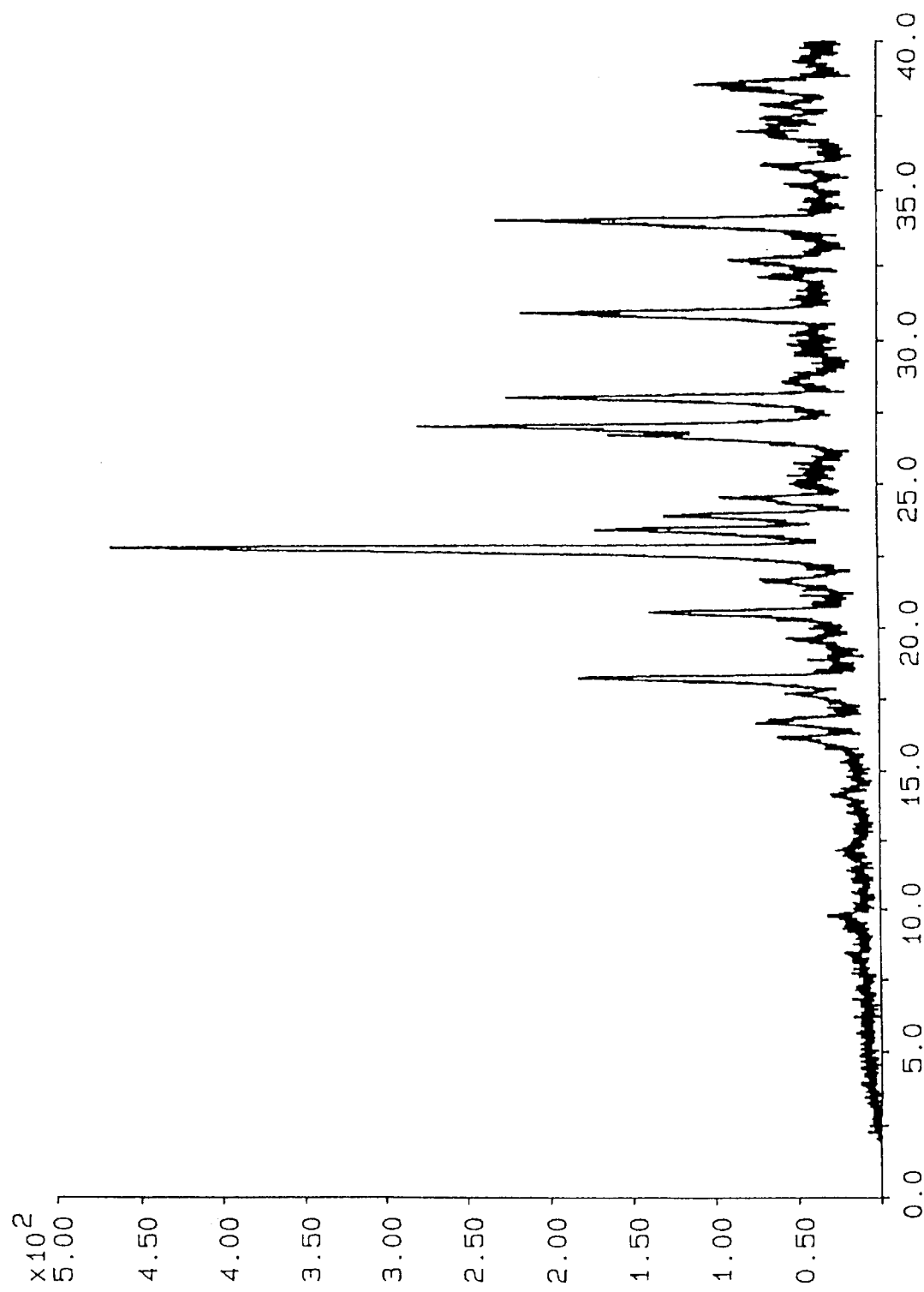
FIG. 1 is an X-Ray Powder Diffraction pattern of Compound I, in unsolvated form.

The compound has the following structural formula:

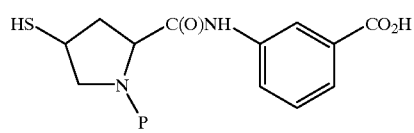

wherein P represents H or a protecting group.

The salt form of the compound can be protonated as shown in the following:

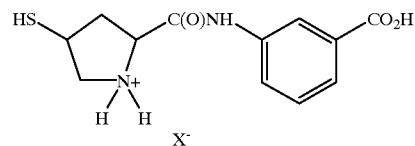

wherein $X^-$ represents a negatively charged counterion. The salt forms can also be present in the form of a solvate.

The crystalline forms of the compound are characterized below by virtue of their X-Ray Powder Diffraction (XRPD) patterns. The XRPD patterns were collected on a Philips APD 3720 automated powder diffractometer. The x-ray generator employed a copper target, an accelerating potential of 45 kV and a filament emission of 40 mA. Diffraction patterns were collected from 2° C. to 40° C.

The hydrochloride salt of the compound (unsolvated material) was characterized as having an XRPD pattern at 5.5, 5.3, 4.9, 4.3, 4.1, 3.9, 3.8, 3.7, 3.6, 3.3, 3.2, 2.9, 2.6 and 2.3 angstroms. More complete XRPD data pertaining to the compound is shown below in Table 1.

TABLE 1

| Peak No. | Angle (deg) | Tip Width (deg) | Peak (cts) | Backg (cts) | D Spac (Ang) | I/Imax (%) | A1 | A2 | Ot | Sign |
|---|---|---|---|---|---|---|---|---|---|---|
| 1 | 8.3325 | 0.48 | 10. | 6. | 10.6028 | 2.34 | x | x | | 0.83 |
| 2 | 9.7600 | 0.12 | 19. | 7. | 9.0550 | 4.43 | x | x | | 0.89 |
| 3 | 12.1375 | 0.36 | 10. | 8. | 7.2861 | 2.34 | x | x | | 1.05 |
| 4 | 14.1525 | 0.15 | 17. | 9. | 6.2529 | 3.85 | x | x | | 0.91 |
| 5 | 16.1575 | 0.15 | 46. | 12. | 5.4812 | 10.59 | x | x | | 2.09 |
| 6 | 16.6450 | 0.15 | 53. | 12. | 5.3218 | 12.20 | x | x | | 1.02 |
| 7 | 16.8200 | 0.15 | 41. | 12. | 5.2668 | 9.38 | x | x | | 0.91 |
| 8 | 17.6250 | 0.24 | 30. | 13. | 5.0280 | 6.93 | x | x | | 1.26 |
| 9 | 18.2600 | 0.07 | 154. | 13. | 4.8546 | 35.20 | x | x | | 1.38 |
| 10 | 18.9025 | 0.18 | 17. | 14. | 4.6910 | 3.85 | x | x | | 1.26 |
| 11 | 19.5625 | 0.12 | 34. | 14. | 4.5342 | 7.70 | x | x | | 0.76 |
| 12 | 20.5175 | 0.09 | 117. | 15 | 4.3252 | 26.70 | x | x | | 1.07 |
| 13 | 21.6225 | 0.21 | 48. | 16 | 4.1066 | 10.90 | x | x | | 2.88 |
| 14 | 22.6875 | 0.13 | 437. | 17 | 3.9162 | 100.00 | x | x | | 5.62 |
| 15 | 23.4200 | 0.09 | 12&. | 18 | 3.7954 | 29.23 | x | x | | 0.78 |
| 16 | 23.8750 | 0.18 | 96. | 18 | 3.7241 | 21.99 | x | x | | 3.47 |
| 17 | 24.4900 | 0.12 | 72. | 18 | 3.6319 | 16.54 | x | x | | 3.02 |
| 18 | 25.0125 | 0.18 | 26. | 18 | 3.5572 | 5.95 | x | x | | 0.89 |
| 19 | 25.7275 | 0.18 | 20. | 19 | 3.4599 | 4.64 | x | x | | 0.83 |
| 20 | 26.6250 | 0.18 | 114. | 20 | 3.3453 | 26.21 | x | x | | 2.09 |
| 21 | 26.9725 | 0.09 | 246. | 20 | 3.3030 | 56.43 | x | x | | 1.74 |
| 22 | 27.9675 | 0.07 | 202. | 21 | 3.1877 | 46.16 | x | x | | 1.32 |
| 23 | 28.5925 | 0.24 | 30. | 22 | 3.1194 | 6.93 | x | x | | 1.05 |

TABLE 1-continued

| Peak No. | Angle (deg) | Tip Width (deg) | Peak (cts) | Backg (cts) | D Spac (Ang) | I/Imax (%) | A1 | A2 | Ot | Sign |
|---|---|---|---|---|---|---|---|---|---|---|
| 24 | 30.8400 | 0.07 | 196. | 24 | 2.8970 | 44.87 | x | x | | 1.55 |
| 25 | 32.1275 | 0.18 | 38. | 24 | 2.7838 | 8.80 | x | x | | 1.82 |
| 26 | 32.6325 | 0.18 | 58. | 25 | 2.7419 | 13.22 | x | x | | 2.04 |
| 27 | 33.9250 | 0.18 | 174. | 26 | 2.6403 | 39.89 | x | x | | 5.13 |
| 28 | 35.1000 | 0.18 | 17. | 27 | 2.5546 | 3.85 | x | x | | 1.05 |
| 29 | 35.7950 | 0.24 | 32. | 27 | 2.5065 | 7.44 | x | x | | 3.16 |
| 30 | 36.8400 | 0.36 | 37. | 28 | 2.4378 | 8.52 | x | x | | 2.45 |
| 31 | 37.3975 | 0.15 | 35. | 28 | 2.4027 | 7.97 | x | x | | 1.07 |
| 32 | 37.8050 | 0.15 | 35. | 28 | 2.3778 | 7.97 | x | x | | 1.15 |
| 33 | 38.5300 | 0.12 | 69. | 29 | 2.3347 | 15.77 | x | x | | 1.15 |

Notes:
Generator settings: 45kV, 40 mA
Cu alpha1, 2 wave lengths 1.54060, 1.54439 Ang
Step size, sample time 0.015 deg, 0.20 s, 0.075 deg/s
Monochromator used
Divergence slit Automatic (irradiated sample length 12.5 mm)
Peak angle range 2.007–40.002 deg
Range in D spacing 2.25207–43.9723 Ang
Peak position criterion Top of smoothed data
Cryst peak width range 0.00–2.00 deg
Minim peak significance 0.75
Number of peaks in file 33 (alpha1: 33, amorphous: 0)
Maximum intensity 437. cts, 2184. 1 cps The XRPD pattern corresponding to Table I is shown as FIG. 1.

Figure 2:
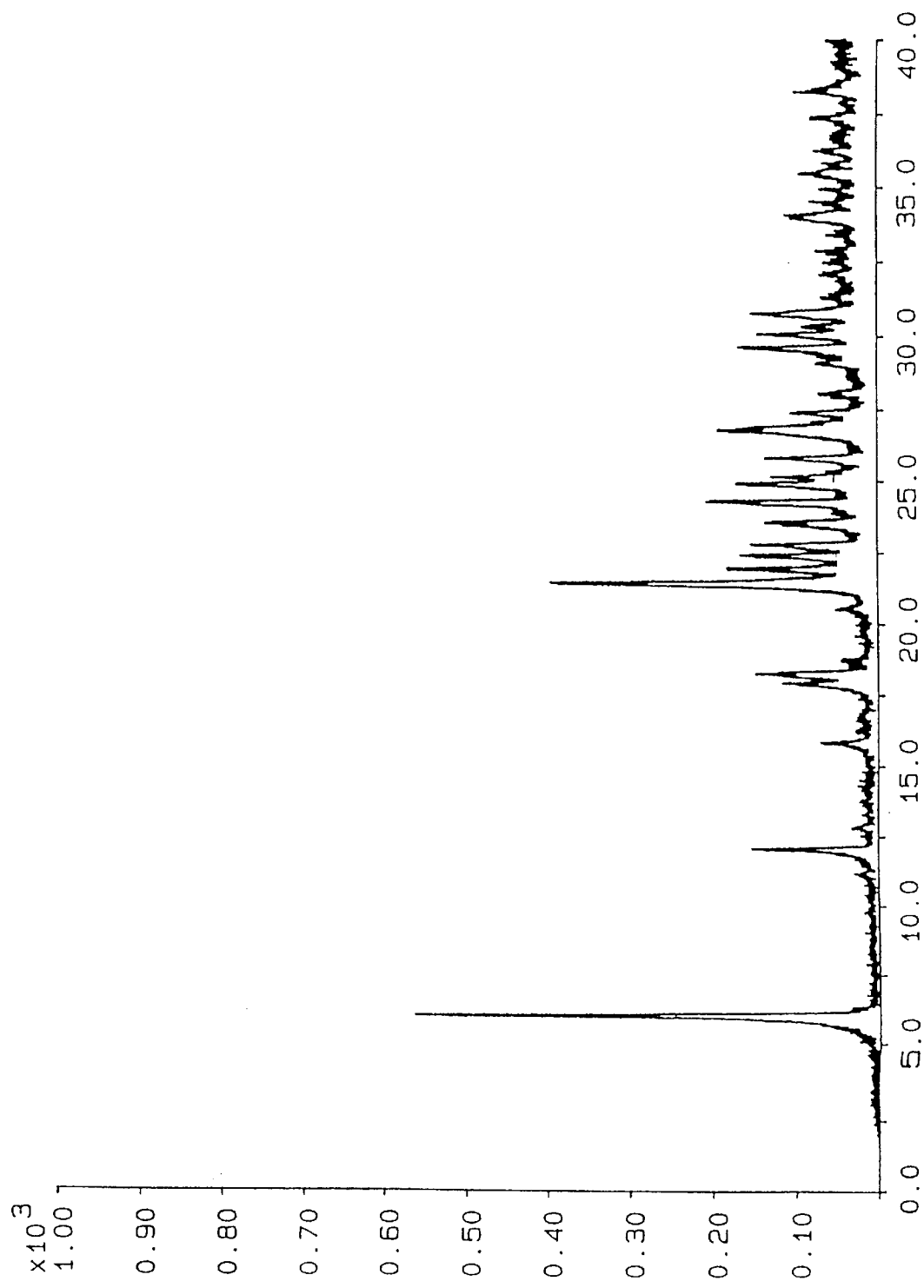
FIG. 2 is an X-Ray Powder Diffraction pattern of Compound I as the 1-butanol solvate.

The hydrochloride salt 1-butanol solvate was shown to exhibit patterns such as the ERPD pattern shown as FIG. 2. Characteristic D-spacings are 14.6, 7.3, 5.6, 4.9, 4.2, 4.0, 3.9, 3.8, 3.7, 3.6, 3.5, 3.3, 3.0 and 2.9 Ang. More complete XRPD data pertaining to the solvate is shown below in Table 2.

TABLE 2

| Peak No. | Angle (deg) | Tip Width (deg) | Peak (cts) | Backg (cts) | D Spac (Ang) | I/Imax (%) | A1 | A2 | Ot | Sign |
|---|---|---|---|---|---|---|---|---|---|---|
| 1 | 3.0625 | 0.72 | 10 | 0. | 28.8263 | 1.84 | x | x | | 1.20 |
| 2 | 6.0675 | 0.07 | 557 | 4. | 14.5548 | 100.00 | x | x | | 5.75 |
| 3 | 9.7950 | 0.18 | 10. | 5. | 9.0227 | 1.84 | x | x | | 0.85 |
| 4 | 11.1825 | 0.15 | 14. | 6. | 7.9061 | 2.59 | x | x | | 1.10 |
| 5 | 12.0625 | 0.09 | 135. | 6. | 7.3312 | 24.16 | x | x | | 3.09 |
| 6 | 12.8450 | 0.12 | 19. | 7. | 6.8863 | 3.48 | x | x | | 1.12 |
| 7 | 15.8225 | 0.07 | 62. | 8. | 5.5965 | 11.21 | x | x | | 1.35 |
| 8 | 16.7900 | 0.30 | 12. | 10. | 5.2761 | 2.08 | x | x | | 0.95 |
| 9 | 17.9150 | 0.07 | 98. | 10. | 4.9473 | 17.60 | x | x | | 1.17 |
| 10 | 18.2525 | 0.21 | 119. | 11. | 4.8566 | 21.33 | x | x | | 6.46 |
| 11 | 18.7050 | 0.09 | 30. | 11. | 4.7401 | 5.43 | x | x | | 1.29 |
| 12 | 20.5575 | 0.09 | 31. | 13. | 4.3169 | 5.63 | x | x | | 1.32 |
| 13 | 21.3925 | 0.12 | 376. | 13. | 4.1503 | 67.57 | x | x | | 7.08 |
| 14 | 21.9375 | 0.06 | 159. | 14. | 4.0484 | 28.50 | x | x | | 0.81 |
| 15 | 22.3975 | 0.12 | 144. | 14. | 3.9663 | 25.85 | x | x | | 4.07 |
| 16 | 22.7650 | 0.06 | 132. | 15. | 3.9031 | 23.74 | x | x | | 1.23 |
| 17 | 23.5475 | 0.07 | 114. | 16. | 3.7751 | 20.56 | x | x | | 1.10 |
| 18 | 24.2675 | 0.06 | 180. | 17. | 3.6647 | 32.24 | x | x | | 1.02 |
| 19 | 24.8675 | 0.09 | 149. | 17. | 3.5776 | 26.72 | x | x | | 2.04 |
| 20 | 25.1500 | 0.06 | 98. | 18. | 3.5381 | 17.60 | x | x | | 0.79 |
| 21 | 25.8000 | 0.07 | 108. | 18. | 3.4504 | 19.42 | x | x | | 1.35 |
| 22 | 26.7525 | 0.12 | 159. | 18. | 3.3297 | 28.50 | x | x | | 1.17 |
| 23 | 27.3775 | 0.07 | 77. | 19. | 3.2551 | 13.90 | x | x | | 0.93 |
| 24 | 28.0575 | 0.15 | 37. | 20. | 3.1777 | 6.68 | x | x | | 1.51 |
| 25 | 29.0475 | 0.15 | 45. | 20. | 3.0716 | 8.06 | x | x | | 1.41 |
| 26 | 29.5925 | 0.10 | 142. | 21. | 3.0163 | 25.43 | x | x | | 2.63 |
| 27 | 30.0575 | 0.06 | 117. | 22. | 2.9706 | 20.94 | x | x | | 0.78 |
| 28 | 30.3500 | 0.12 | 58. | 22. | 2.9427 | 10.37 | x | x | | 0.93 |
| 29 | 30.7375 | 0.24 | 117. | 23. | 2.9065 | 20.94 | x | x | | 7.76 |
| 30 | 31.3225 | 0.18 | 30. | 23. | 2.8535 | 5.43 | x | x | | 1.38 |
| 31 | 32.0950 | 0.12 | 35. | 24. | 2.7866 | 6.25 | x | x. | | 0.87 |
| 32 | 32.8725 | 0.18 | 25. | 24. | 2.7224 | 4.49 | x | x | | 1.07 |
| 33 | 33.4025 | 0.24 | 18. | 25. | 2.6804 | 3.32 | x | x | | 0.85 |
| 34 | 33.9575 | 0.24 | 76. | 26. | 2.6379 | 13.59 | x | x | | 4.37 |

TABLE 2-continued

| Peak No. | Angle (deg) | Tip Width (deg) | Peak (cts) | Backg (cts) | D Spac (Ang) | I/Imax (%) | Type | | | Sign |
|---|---|---|---|---|---|---|---|---|---|---|
| | | | | | | | A1 | A2 | Ot | |
| 35 | 34.5225 | 0.04 | 42. | 26. | 2.5960 | 7.59 | x | x | | 0.76 |
| 36 | 34.9325 | 0.06 | 37. | 27. | 2.5664 | 6.68 | x | x | | 0.78 |
| 37 | 35.4450 | 0.09 | 67. | 27. | 2.5305 | 12.07 | x | x | | 1.45 |
| 38 | 36.2300 | 0.21 | 36. | 28. | 2.4774 | 6.46 | x | x | | 2.88 |
| 39 | 37.3500 | 0.12 | 49. | 29. | 2.4057 | 8.80 | x | x | | 1.38 |
| 40 | 38.2150 | 0.12 | 52. | 29. | 2.3532 | 9.31 | x | x | | 1.20 |

Notes:
Generator settings: 45kV, 40 mA
Cu alpha1, 2 wavelengths 1.54060, 1.54439 Ang
Step size, sample time 0.015 deg, 0.20 s, 0.075 deg/s
Monochromator used
Divergence slit Automatic (irradiated sample length 12.5 mm)
Peak angle range 2.007–40.002 deg
Range in D spacing 2.25207–43.9723 Ang
Peak position criterion Top of smoothed data
Cryst peak width range 0.00–2.00 deg
Minim peak significance 0.75
Number of peaks in file 33 (alpha1: 33, amorphous: 0)
Maximum intensity 437. cts, 2184. 1 cps The XRPD pattern corresponding to Table 2 is shown as FIG. 2.

Solid material which was exposed to acetic acid was characterized as having an XRPD pattern at 5.4, 5.3, 5.1, 4.2, 3.8, 3.6, 3.4, 3.1, 2.7 and 2.6 angstroms. More complete XRPD data pertaining to the solvate is shown below in Table 3.

TABLE 3

| Peak No. | Angle (deg) | Tip Width (deg) | Peak (cts) | Backg (cts) | D Spac (Ang) | I/Imax (%) | Type | | | Sign |
|---|---|---|---|---|---|---|---|---|---|---|
| | | | | | | | A1 | A2 | Ot | |
| 1 | 3.1400 | 0.96 | 10. | −1. | 28.1149 | 2.96 | x | x | | 0.81 |
| 2 | 6.0350 | 0.24 | 12. | 5. | 14.6331 | 3.34 | x | x | | 0.95 |
| 3 | 11.4925 | 0.12 | 32. | 10. | 7.6935 | 9.39 | x | x | | 0.95 |
| 4 | 11.9925 | 0.24 | 48. | 10. | 7.3739 | 13.76 | x | x | | 4.47 |
| 5 | 12.8950 | 0.18 | 17. | 10. | 6.8597 | 4.86 | x | x | | 1.00 |
| 6 | 16.3050 | 0.21 | 202. | 12. | 5.4320 | 58.28 | x | x | | 7.76 |
| 7 | 16.6950 | 0.09 | 86. | 13. | 5.3060 | 25.00 | x | x | | 1.02 |
| 8 | 17.5350 | 0.07 | 130. | 13. | 5.0536 | 37.57 | x | x | | 0.95 |
| 9 | 18.0250 | 0.09 | 38. | 14. | 4.9173 | 11.11 | x | x | | 0.98 |
| 10 | 20.0125 | 0.24 | 37. | 16. | 4.4332 | 10.76 | x | x | | 1.70 |
| 11 | 20.4650 | 0.09 | 56. | 16. | 4.3362 | 16.26 | x | x | | 1.12 |
| 12 | 21.0225 | 0.10 | 149. | 17. | 4.2225 | 43.02 | x | x | | 1.95 |
| 13 | 21.8425 | 0.06 | 81. | 18. | 4.0658 | 23.41 | x | x | | 0.85 |
| 14 | 23.2675 | 0.33 | 346. | 19. | 3.8199 | 100.00 | x | x | | 21.88 |
| 15 | 23.9075 | 0.30 | 77. | 19. | 3.7191 | 22.38 | x | x | | 1.58 |
| 16 | 24.8525 | 0.09 | 216. | 21. | 3.5797 | 62.46 | x | x | | 1.02 |
| 17 | 25.9625 | 0.30 | 213. | 22. | 3.4292 | 61.61 | x | x | | 12.02 |
| 18 | 26.5600 | 0.30 | 110. | 23. | 3.3534 | 31.87 | x | x | | 2.45 |
| 19 | 27.3000 | 0.18 | 48. | 23. | 3.2641 | 13.76 | x | x | | 0.79 |
| 20 | 27.4900 | 0.36 | 42. | 23. | 3.2420 | 12.21 | x | x | | 0.85 |
| 21 | 28.2425 | 0.18 | 29. | 24. | 3.1573 | 8.43 | x | x | | 0.76 |
| 22 | 28.9025 | 0.09 | 62. | 25. | 3.0867 | 18.04 | x | x | | 1.07 |
| 23 | 29.7375 | 0.18 | 38. | 26. | 3.0019 | 11.11 | x | x | | 1.17 |
| 24 | 30.3075 | 0.15 | 28. | 26. | 2.9467 | 8.12 | x | x | | 1.00 |
| 25 | 31.2550 | 0.18 | 32. | 27. | 2.8595 | 9.39 | x | x | | 0.78 |
| 26 | 32.9850 | 0.30 | 83. | 29. | 2.7134 | 23.94 | x | x | | 3.24 |
| 27 | 33.3150 | 0.18 | 62. | 29. | 2.6872 | 18.04 | x | x | | 0.81 |
| 28 | 33.9350 | 0.09 | 48. | 30. | 2.6396 | 13.76 | x | x | | 1.02 |
| 29 | 34.4175 | 0.15 | 74. | 30. | 2.6036 | 21.38 | x | x | | 1.91 |
| 30 | 35.0900 | 0.36 | 42. | 31. | 2.5553 | 12.21 | x | x | | 2.40 |
| 31 | 35.9900 | 0.36 | 40. | 32. | 2.4934 | 11.47 | x | x | | 2.14 |

TABLE 3-continued

| Peak No. | Angle (deg) | Tip Width (deg) | Peak (cts) | Backg (cts) | D Spac (Ang) | I/Imax (%) | A1 | A2 | Ot | Sign |
|---|---|---|---|---|---|---|---|---|---|---|
| 32 | 37.0675 | 0.30 | 62. | 34. | 2.4234 | 18.04 | x | x | | 1.78 |
| 33 | 38.4225 | 0.24 | 41. | 35. | 2.3410 | 11.84 | x | x | | 0.95 |

Figure 3:
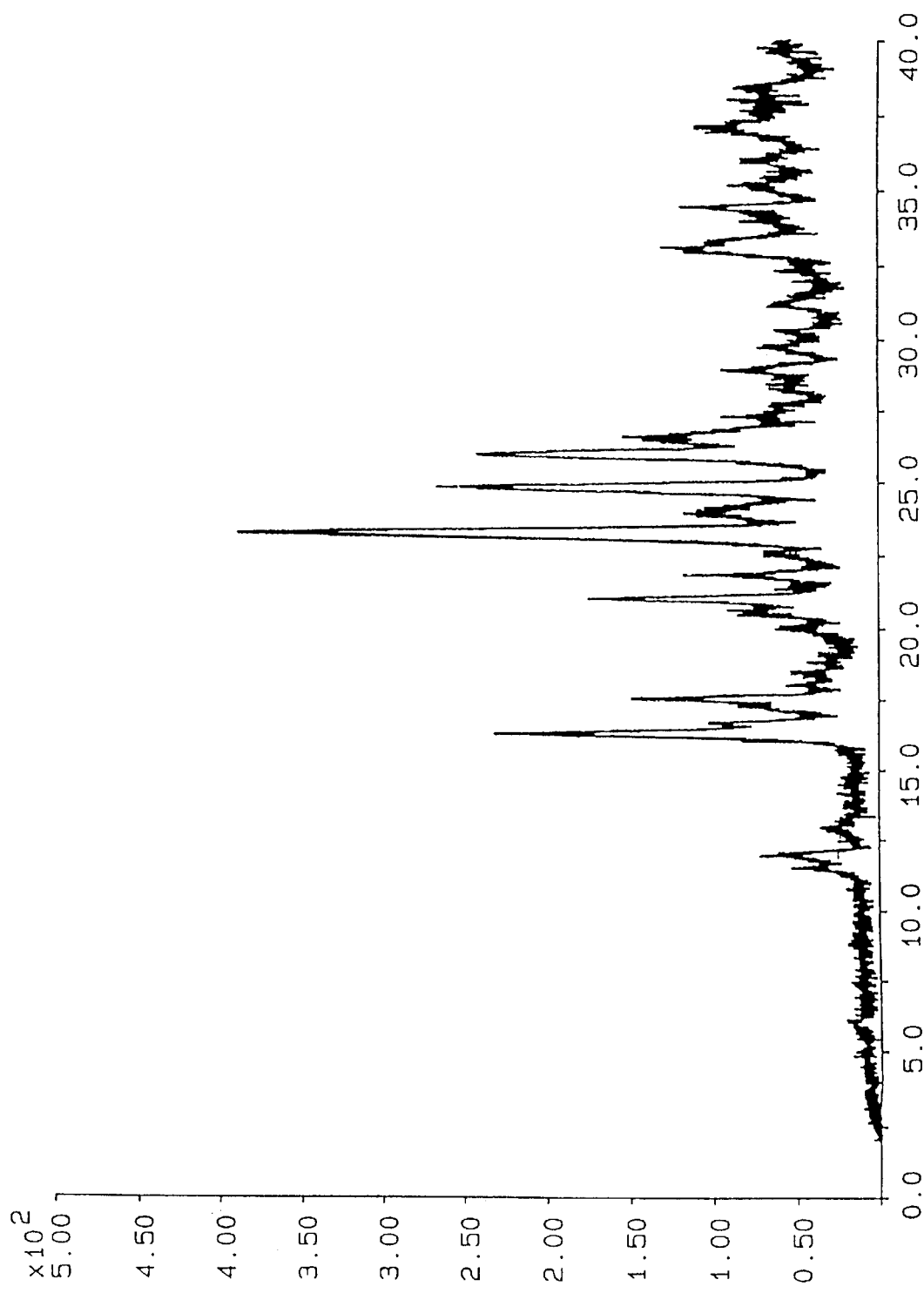
FIG. 3 is an X-Ray Powder Diffraction pattern of Compound I, as the acetic acid solvate.

Notes:
Generator settings: 45kV, 40 mA
Cu alpha1, 2 wavelengths 1.54060, 1.54439 Ang
Step size, sample time 0.015 deg, 0.20 s, 0.075 deg/s
Monochromator used
Divergence slit Automatic (irradiated sample length 12.5 mm)
Peak angle range 2.007–40.002 deg
Range in D spacing 2.25207–43.9723 Ang
Peak position criterion Top of smoothed data
Cryst peak width range 0.00–2.00 deg
Minim peak significance 0.75
Number of peaks in file 33 (alpha1: 33, amorphous: 0)
Maximum intensity 437. cts, 2184.1 cps The XRPD pattern corresponding to Table 3 is shown as FIG. 3.

The crystalline compound of the present invention is useful in various pharmaceutically acceptable salt forms, for the synthesis of carbapenem compounds that are in turn useful for the treatment of bacterial infections in animal and human subjects. The term "pharmaceutically acceptable salt" refers to those salt forms which would be apparent to the pharmaceutical chemist. i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity and flowability of the resulting bulk drug.

Typically the intermediate compound is protonated, and is found in association with a negatively charged counterion, represented by the generic $X^-$. There are various possibilities for the charge balancing counterion $X^-$. Representative examples of such counterions are the following: acetate, adipate, aminosalicylate, anhydromethylenecitrate, ascorbate, aspartate, benzoate, benzenesulfonate, bicarbonate, bisulfate, bromide, citrate, camphorate, camphorsulfonate, carbonate, chloride, digluconate, edetate, edisylate, estolate, ethanesulfonate, fumarate, glucoheptanoate, gluconate, glutamate, glycerophosphate, glycolate, hydroxynaphthoate, 2-hydroxyethanesulfonate, iodide, lactate, lactobionate, malate, maleate, mandelate, methylenebis(salicylate), mucate, methanesulfonate, napadisylate, napsylate, pamoate, pantothenate, pectinate, phosphate/diphosphate, polygalacturonate, propionate, salicylate, stearate, succinate, sulfate, tartrate, triflate, tosylate and undecanoate. Other anionic species will be apparent to the ordinarily skilled chemist.

The preferred form of the crystalline compound is the hydrochloride salt form.

The compound can be produced in accordance with the following non-limiting examples.

EXAMPLE ONE

A. Synthesis

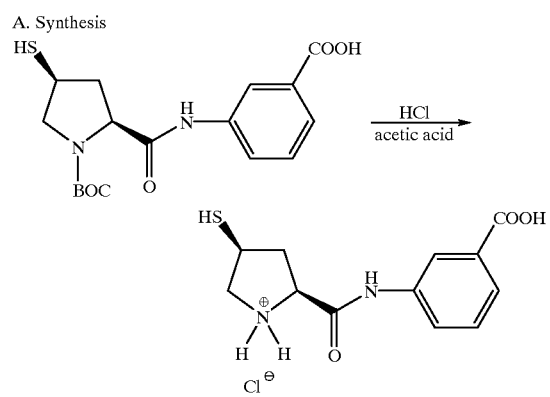

The BOC protected sidechain 1 (prepared according to the teachings of PCT WO97/06154 published on Feb. 20, 1997) was dissolved in 1.5 L of a 1 N solution of dry hydrogen chloride in acetic acid (30 min). Gas evolution was observed and the reaction product slowly crystallized. After filtering, washing (with acetic acid and hexane) and drying 137 g of product was obtained. The crystals contain acetic acid but are not a solvate.

B. Recrystallization Procedures

1-Propanol Solvate

The above product (25 g) was dissolved in 1-propanol (500 mL) at 100° C. Upon cooling the product crystallized out. After filtering, washing (with 1-propanol and hexane) and drying 20 g of the 1-propanol solvate was obtained.

1-Butanol Solvate

The above product (25 g) was dissolved in a mixture of 1-butanol (225 mL) and water (25 mL) at RT. The resulting solution was concentrated in vacuo to a total volume of 125 mL and seeded with authentic 1-butanol solvate. The crystals were filtered, washed (with 1-butanol and hexane) and dried at RT to give 25 g of the 1-butanol solvate.

Acetic Acid Solvate

The above product was slurried overnight in a 95/5 mixture of acetic acid and water at RT and then partially concentrated via distillation in vacuo. The crystals were filtered, washed (with acetic acid and hexane) and dried to give the acetic acid solvate.

What is claimed is:

1. Crystalline 2S-cis-3-[[(4-mercapto-2-pyrrolidinyl)carbonyl]amino]benzoic acid or a pharmaceutically acceptable salt or solvate thereof.

2. Crystalline 2S-cis-3-[[(4-mercapto-2-pyrrolidinyl)carbonyl]amino]benzoic acid in accordance with claim 1, having an X-ray powder diffraction pattern in accordance with FIG. 1, 2 or 3.

3. Crystalline 2S-cis-3-[[(4-mercapto-2-pyrrolidinyl)carbonyl]amino]benzoic acid in accordance with claim 1 as the hydrochloride salt.

4. Crystalline 2S-cis-3-[[(4-mercapto-2-pyrrolidinyl)carbonyl]amino]benzoic acid in accordance with claim 3 as the hydrochloride salt unsolvated form.

5. Crystalline 2S-cis-3-[[(4-mercapto-2-pyrrolidinyl)carbonyl]amino]benzoic acid in accordance with claim 3 as the hydrochloride salt 1-butanol solvate.

6. Crystalline 2S-cis-3-[[(4-mercapto-2-pyrrolidinyl)carbonyl]amino]benzoic acid in accordance with claim 3 as the hydrochloride salt acetic acid solvate.

7. Crystalline 2S-cis-3-[[(4-mercapto-2-pyrrolidinyl)carbonyl]amino]benzoic acid in accordance with claim 1, having one of the following X-ray powder diffraction patterns:

TABLE

| d - Spacings (Å) - HCl salt | | |
| --- | --- | --- |
| Unsolvated | 1-butanol solvate | Acetic acid solvate |
| 5.5 | 14.6 | 5.4 |
| 5.3 | 7.3 | 5.3 |
| 4.9 | 5.6 | 5.1 |
| 4.3 | 4.9 | 4.2 |
| 4.1 | 4.2 | 3.8 |
| 3.9 | 4.0 | 3.6 |
| 3.8 | 3.9 | 3.4 |
| 3.7 | 3.8 | 3.1 |
| 3.6 | 3.7 | 2.7 |
| 3.3 | 3.6 | 2.6 |
| 3.2 | 3.5 | |
| 2.9 | 3.3 | |
| 2.6 | 3.0 | |
| 2.3 | 2.9 | |

* * * * *